United States Patent [19]

Andersson et al.

[11] 4,022,758

[45] May 10, 1977

[54] ISOLATION OF COAGULATION FACTORS I AND VIII FROM BIOLOGICAL MATERIAL

[75] Inventors: Lars-Olov Andersson, Knivsta; Håkan Gunnar Borg, Huddinge; Nanna Forsman; Gunnar Hanshoff, both of Jarfalla; Göran Lindroos, Stockholm; Maggie Miller-Andersson, Jarfalla; Elisabeth Charlotte Carling nee Ehrenberg, Dalby, all of Sweden

[73] Assignee: AB Kabi, Stockholm, Sweden

[22] Filed: July 30, 1975

[21] Appl. No.: 598,322

Related U.S. Application Data

[62] Division of Ser. No. 371,491, June 19, 1973, Pat. No. 3,920,625.

[52] U.S. Cl. .......................................... 260/112 B
[51] Int. Cl.$^2$ ........................................... H23J 1/06
[58] Field of Search ............... 260/112 B; 424/101, 424/117

[56] References Cited

UNITED STATES PATENTS

| 2,543,808 | 3/1951 | Seegers | 260/112 B |
| 3,631,018 | 12/1971 | Shanbrom | 260/112 B |
| 3,652,530 | 3/1972 | Johnson | 260/112 B |
| 3,803,115 | 4/1974 | Fekete | 260/112 B |
| 3,842,061 | 10/1974 | Andersson | 260/112 B |

OTHER PUBLICATIONS

Chemical Abstracts, vol. 77, No. 71654s, Weiss, 1972.

Primary Examiner—Paul R. Michl

[57] ABSTRACT

The blood coagulation factors I (fibrinogen) and VIII (antihemophilia factor, abbreviated AHF) are isolated in high yields from animal tissue materials such as blood or blood products (e.g. plasma) or plasma fractions by a procedure involving the essential step of adsorption (as in affinity chromatography) of at least one of these factors, in a liquid system, onto a water-insoluble gel matrix primarily composed of a cross-linked sulfated or sulfonated, gel-forming carbohydrate such as cross-linked dextran sulfate-agarose, cross-linked dextran sulfate-dextran, cross-linked heparin-agarose and other such gel matrix-providing substances.

15 Claims, No Drawings

ISOLATION OF COAGULATION FACTORS I AND VIII FROM BIOLOGICAL MATERIAL

This application is a divisional of copending application Ser. No. 371,491 filed June 19, 1973 now U.S. Pat. No. 3,920,625.

This invention is that of isolating blood coagulation factors I (fibrinogen) and VIII (antihemophilia factor, abbreviated AHF) in high yields from animal tissue materials such as blood or blood products (e.g. plasma) or plasma fractions by a procedure involving the essential step of adsorption (as in affinity chromatography) of at least one of these factors, in a liquid system, onto a water-insoluble gel matrix primarily composed of a cross-linked sulfated or sulfonated, gel-forming carbohydrate such as cross-linked dextran sulfate-agarose, cross-linked dextran sulfate-dextran, cross-linked heparin-agarose and other such gel matrix-providing substances, e.g. benzidine-2,2′-disulfonic acid-agarose.

Considerable work has been performed throughout the years in seeking to recognize the mechanisms of blood coagulation and to isolate the participating components. The great interest in the coagulation of blood can be accounted for partly by the purely scientific concern about the system as such. However, first of all, knowledge of how the coagulation of blood takes place and how it can be influenced is extremely important from a clinical point of view. There are still a number of unclear points concerning the mechanisms of blood coagulation, but there is unanimity that blood coagulation may be described as a process wherein activation of a trace component is followed by successive activation of a number of components, which eventually results in the formation of a clot. A relatively small initial effect thus results in a valuable final effect depending on the multiplying effect which exists in the system.

However, only a few of the various components participating in the blood coagulation system have so far been isolated in pure state. These components usually are called coagulation factors, and are presumed to be 12 in number, with each designated by its respective Roman numeral, i.e. factor I, factor II, and so on, according to the nomenclature established by the International Commission on Haemostasis and Thrombosis (Thromb. Diathes, Haemorrhag. Suppl. 13, 1964).

In connection with the blood coagulation factors there is reason also to mention two other systems. One of them is the system of inhibitors, which regulates the tendency of the blood to coagulate and prevents the formation of thrombi. This system contains, among others antithrombin III, factor $X_a$ inhibitor, and factor $XI_a$ inhibitor. The other one is the system which attends to the dissolution of possible thrombi, and usually is called the fibrinolytic system. It contains plasmin and plasminogen as important components.

Coagulation factor I, i.e. fibrinogen, is (i) the structural element that forms the gel that results from the coagulation of blood or plasma, and (ii) a protein with a molecular weight of about 340,000. Its concentration in the plasma is about 2 mg./ml. of plasma. During the blood coagulation process an enzyme is formed, namely, thrombin which hydrolytically splits off two peptides from the fibrinogen. The splitting-off of these peptides from the fibrinogen causes the latter to alter its structure and as altered to start aggregating. This aggregation results in the formation of a gel, i.e. a clot.

Fibrinogen is used clinically to stop certain types of bleeding. It is relatively difficult to produce fibrinogen for clinical use. Since fibrinogen is a relatively sensitive molecule, the fractionation methods in its production have to be very mild. The greatest difficulty is to obtain a quality of fibrinogen with high coagulability and which at the same time manifests good stability in aqueous solution.

Coagulation factor VIII, the antihemophilia factor (briefly called AHF), is a protein with a molecular weight of about 1 million. It is present in very small amounts in blood plasma, its normal concentration being about 10 µg./ml. of plasma. One of the most known hereditary coagulation defects is characterized by the absence of the biologically active factor VIII (AHF). This defect is the classical hemophilia or hemophilia A. Heavy hemophilia manifests itself as a strongly increased bleeding tendency where the least wound may give rise to a mortal bleeding.

This disease manifests itself even at a very young age, and many different types of complications may occur. Quite usually the patients get repeated joint bleedings leading to inflammations (at joints) and in the long run to invalidism. This causes most of the grave hemophiliacs to be heavily motility-wise disturbed even at the age of 20 years if they have not been treated with preparations containing AHF.

The therapy which can be used in hemophilia is transfusion of whole (human) blood or plasma and even various concentrates containing AHF. The medicinal advantages of using such concentrates are obvious. The AHF concentrates presently available can be divided into two different types, partly high concentrated and partly low concentrated preparations. The preparations mostly used heretofore are of the low concentrated type. Examples of them are cryoprecipitates according to Pool (Pool J., Hershgold, E. K., Pappenhagen, A., Nature 203 (1964) page 312), and Cohn fraction I-O (described in Blomback, M. Arkiv Kemi 12 (1958) page 387).

Both of these AHF low concentrate preparations contain considerable amounts of fibrinogen. The disadvantage with this type of preparation is that the patients need administration of relatively large quantities of an aqueous solution of it by infusion. Lately certain so called highly concentrated AHF preparations have been developed. With these an adequate dose of AHF can be given in an aqueous solution volume of from 10 to 15 ml. This type of AHF concentrate is considerably easier to use than the earlier type.

Clinically the highly concentrated preparations seem to function well, but there also are certain disadvantages with them. From an isolation standpoint a disadvantage with them is that the yield of AHF-activity from the starting plasma is relatively low. Furthermore, the other portions which occur in the fractions from which AHF is recovered generally are not utilized. Finally, these methods require a very high grade starting material, i.e., the blood plasma should be fresh or frozen immediately after the collection of the blood and subsequent centrifugation.

Coagulation factor IX, also known as B-factor because one type of hemophilia, namely, hemophilia B, is caused by hereditary deficiency of the coagulation factor IX. Hemophilia B manifests itself as a strongly increased bleeding tendency at trauma and surgical interventions. In grave cases large subcutaneous and intramuscular haematoma may occur. Junction bleedings with secondary junction deformities resulting in invalidism also is a rather common condition in connection with hemophilia B. The treatment which can be given is any of various forms of substitutional therapy, namely, transfusion of blood, plasma or some of the now available factor IX concentrates.

The present invention makes it possible to eliminate the above-mentioned disadvantages. The various procedures embraced by the invention for isolating the coagulation factors I and VIII, have in common that they include the essential novel step of adsorbing one or both of them, from an aqueous liquid system onto an adsorption medium which is a sulfated, or sulfonate group-containing, cross-linked gel matrix-forming carbohydrate. Thus, these are bound on the gel and purified in this way. In the purification or isolation of coagulation factor VIII, the sulfated gel matrix is used to adsorb the dominating fraction i.e. fibrinogen, from the starting material.

Runs using blood plasma as the starting material showed that under suitable conditions factor I and factor IX could be induced to be bound almost quantitatively on the heparin-containing agarose gel, i.e. each of these factors separately.

Each of these factors I and IX respectively then is eluted by contacting the adsorbate-holding gel with a buffer differing in composition from that wherein the protein material was dissolved. Variations occur in the purity of the starting protein fractions. However, considerably better results were obtained when using as the starting material the Cohn fraction I paste (Journal of the American Chemical Society, 1946, volume 48 page 459).

It is a feature of the invention that both coagulation factor I and factor VIII can be isolated, so to speak, sequentially from the same starting material, such as from Cohn fraction I-O or a cryoprecipitate (Pool et al., above). For example, runs conducting on this phase of the invention using dextran sulfate-agarose (the agarose specifically as SEPHAROSE 4B, a beaded agarose gel prepared by allowing a 4% aqueous solution of agarose to gel in bead form, a product of Pharmacia Fine Chemicals of Piscataway, N.J., U.S.A., and of Uppsala, Sweden) showed that it was possible to adsorb the main part of the fibrinogen on the gel and to have the AHF-activity left in the (non-adsorbed) solution almost quantitatively.

Thereafter the gel is separated, and the AHF left in the solution is precipitated by known procedures (e.g. as seen above, p. 4 lines 10–12, in Pool, Hershgold and Pappenhagen). Subsequently, a highly concentrated solution of AHF can be obtained by dissolving this precipitate in a small quantity of a buffer protein solvent. The fibrinogen can be eluted from the dextran sulfate-SEPHAROSE gel by a buffer of increased ionic strength (e.g. adding sodium chloride to the composition of the non-adsorbed solution). This fibrinogen can be precipitated later and separated and a highly concentrated solution be prepared from it.

This kind of procedure has many advantages compared with the earlier used procedures for obtaining highly concentrated AHF preparations, for example, above all the AHF yield is significantly higher.

An additional advantage is that in addition to the high yield of AHF, the fibrinogen eluted from the gel matrix in the same overall isolation procedure likewise can be used. A further valuable advantage is that even outdated blood or like blood plasma can be used in this new procedure as the starting material source for the AHF as well as for fibrinogen.

Illustrative of the water-insoluble gel matrixes effective in the process of the invention are those having sulfate groups linked to a gel-forming polysaccharide linked to another polysaccharide moiety such as cross-linked dextran sulfate-agarose, cross-linked dextran sulfate-dextran, cross-linked heparin-agarose, cross-linked chondroitin sulfate-agarose, and cross-linked dextran sulfate epichlorhydrin-agarose, and those composed primarily of benzidine disulfonic acid linked to a polysaccharide moiety such as benzidine-2,2'-disulfonic acid-agarose and benzidine-2,2'-disulfonic acid-dextran. The most common method of preparing these gel matrixes involves providing the cross-linking by use of cyanogen bromide at alkaline pH condition.

Considered broadly, the method of the invention is that of isolating at least one of the blood coagulation factors fibrinogen and the antihemophilia factor VIII, from an animal blood tissue product containing at least either of those factors, by contacting a water-insoluble gel matrix adsorbing agent selected from cross-linked dextran sulfate-dextran, cross-linked dextran sulfate-agarose, cross-linked dextran sulfate epichlorhydrin-agarose, dextran sulfate epichlorhydrin-cross-linked agarose, cross-linked chondroitin sulfate, cross-linked heparin-agarose, cross-linked heparin, cross-linked benzidine-2,2'-disulfonic acid-agarose, and cross-linked benzidine-2,2'-disulfonic acid-dextran, with said animal blood tissue product dissolved in an aqueous medium otherwise inert to the therein dissolved content of the said blood tissue product.

The following examples illustrate, but are not to restrict, the invention:

EXAMPLE 1

AHF and Fibrinogen Isolated from Cohn Fraction I-O by Adsorbing the Fibrinogen on Cross-linked Dextran Sulfate-agarose Gel Preparation of cross-linked dextran sulfate-agarose gel using 'SEPHAROSE 4B' agarose Cyanogen bromide (35 g.) was dissolved in 500 ml. of water followed by addition of 30 g. of dextran sulfate. About 1000 ml. of SEPHAROSE 4B gel and 300 ml. of water were added to them and all were mixed together. The mixture was allowed to stand under agitation, and its pH was constantly kept at 11 for 7 minutes by addition of lye. Thereafter addition of the lye was stopped and the pH was allowed to drop slowly on its own. The agitation was continued for 48 hours at room temperature and followed by washing of the gel. The cross-linked dextran sulfate-SEPHAROSE 4B gel then was ready for use.

Fractionation of Fibrinogen and AHF from Cohn fraction I-O

About 10g. of freeze-dried (i.e. lyophilized) Cohn fraction I-O from fresh frozen plasma, containing about 1,500 units AHF, was dissolved in 1,500 ml. of 0.02 M citrate buffer (for pH 6.8). Dry filtered dextran sulfate-SEPHAROSE 4B gel (1,000 ml.) was added to the solution, and the mixture was agitated for 30 minutes. The gel was then separated and washed with 200 ml. of citrate buffer solution. The non-adsorbed solution and the washing liquid were admixed. Analysis showed this mixed solution to contain 6 percent of the original protein quantity and 65 percent of the AHF-active material of the starting Cohn fraction I-O. The AHF was precipitated by addition of sodium citrate at pH 7.1 to this mixed solution. Dissolution of 0.4 g. of this AHF precipitate in about 35 ml. of glycine-NaCl-phosphate buffer (for pH 6.9) provided a solution with a specific activity of 21 AHF units/ml. The total yield of AHF from the Cohn fraction I-O was 55 percent. Desorption of fibrinogen bound on the gel was effected by elution with 2 M NaCl. The major part of the fibrinogen content of the starting Cohn fraction was regained.

The AHF analyses were carried out according to J. J. Veltkampf et al., Thromb. Diath. Haemorrhag, 19–20 (1968) p. 279. The protein concentration was determined by measuring the UV-adsorption at 280 nm.

EXAMPLE 2

AHF and Fibrinogen from Cohn Fraction I Paste from Outdated Plasma by Adsorbing the Fibrinogen on Dextran Sulfate-ECD-SEPHAROSE GEl ("ECD-SEPHAROSE" Stands for Epichlorhydrin Treated Agarose Beads)

About 1 liter of SEPHAROSE 4B was mixed with 1 liter of 1 M sodium hydroxide and 20 ml. of epichlorhydrin and 5 g. of sodium boro hydride ($NaBH_4$). The mixture was kept at 60° C. under agitation for 1 hour. The gel then was washed with warm water and mixed with 500 ml. of 2M sodium hydroxide solution containing 2.5 g. sodium boro hydride. The mixture was autoclaved at 120° C. for 1 hour. The gel then was washed with 500 ml. of 0.2 M sodium hydroxide solution containing 2.5 g. sodium boro hydride. Glacial acetic acid was slowly added until the pH of the mixture had dropped to about 4. The gel was washed with water and coupled with dextran sulfate by use of cyanogen bromide in the same way as described in Example 1.

Fractionation of Fibrinogen and AHF from Cohn Fraction I Pase

To 1 liter of a solution of Cohn fraction I paste (from outdated plasma) in 0.02 M sodium citrate buffer (for pH 6.8), 1 liter of this cross-linked dextran sulfate-ECD-SEPHAROSE just above prepared gel was added. The mixture was allowed to stand under agitation for 15 minutes followed by decanting the gel (with its bound adsorbate) onto a filter. The starting buffered solution which, before the adsorption step contained about 10 mg. of protein/ml. of solution and 0.5 units AHF/ml., then yielded after the adsorption a non-adsorbed effluent solution which contained 1.4 mg. of protein/ml. and 0.36 AHF-units/ml. From this effluent solution the active AHF-material was precipitated by addition of sodium citrate at pH 7.1. Dissolution of 1 g. of the separated (just above) precipitate in about 20 ml. of the glycine-NaCl-phosphate buffer gave a solution with a specific activity of 16 AHF units/ml. The total yield of AHF was 62 percent.

Desorption of the fibrinogen bound to the gel was done by elution with 2 M sodium chloride solution. More than 90 percent of the fibrinogen was recovered.

EXAMPLE 3

AHF and Fibrinogen from Cryoprecipitate by Initially Adsorbing the Fibrinogen on Cross-Linked Dextran Sulfate-SEPHAROSE Gel Cross-linked dextran sulfate-SEPHAROSE 4B was prepared as in Example 1. To 1 liter of a solution of 10 g. of cryoprecipitate in 0.02 M sodium citrate buffer (for pH 6.8), 1 liter of this dextran sulfate SE-PHAROSE-gel was added. The mixture was agitated for 15 minutes followed by decanting the gel onto a filter and collecting the non-adsorbed solution. The original solution contained about 14 mg. of protein/ml. of the non-adsorbed solution and 0.97 AHF units/liter of solution. The AHF-active material then was precipitated by sodium citrate as earlier described in Examples 1 and 2. Desorption of fibrinogen from the gel was done with 2M NaCl as in Example 1 or 2. Yield of AHF was 65 percent and yield of fibrinogen 82 percent.

EXAMPLE 4

AHF and Fibrinogen from Cohn Fraction I-O by Initial Adsorption of Fibrinogen on Cross-linked Dextran Sulfate-dextran Gel 15 g. of dextran "500" (average molecular weight 500,000) was dissolved in 200 ml. of water. 10 g. of cyanogen bromide was dissolved in 100 ml. of water, following which 5 g. of dextran sulfate 500 were added. The solutions were mixed, and the pH was adjusted to 11 by addition of sodium hydroxide and maintained at this value for 7 minutes with simultaneous agitation of the mixture. The resulting gel that formed was allowed to stand 24 hours under agitation and was then washed with 0.1 M sodium bicarbonate buffer and then with water.

Fractionation of Fibrinogen and AHF from Cohn Fraction I-O

The general fractionation features as described for Example 1 were carried out on Cohn fraction I-O from fresh-frozen plasma used as starting material. This resulted in the just above obtained gel's adsorbing 62 percent of the protein material. The yield of AHF was 90 percent. The fibrinogen was eluted quantitatively with 2 M NaCl.

EXAMPLE 5

AHF and Fibrinogen from Cohn Fraction I-O by Initial Adsorption of the Fibrinogen or Cross-linked Heparin-SEPHAROSE Gel Preparation of Heparin-SEPHAROSE 4B gel 5 g. of cyanogen bromide were dissolved in 100 ml. water, following which 1.5 g. of heparin were added to the solution. About 50 ml. of SEPHAROSE 4B gel and 15 ml. of water were admixed in the first solution. The mixture was allowed to stand under agitation while maintaining the pH constant at 11 for 7 minutes by addition of sodium hydroxide. Thereafter the addition of the lye was stopped and the pH was allowed to drop slowly. The agitation was continued for 48 hours at room temperature following which the gel was washed similar to Example 4.

Fractionation of Fibrinogen and AHF from Cohn Fraction I-O

To 30 ml. of a solution of freeze-dried Cohn fraction I-O from fresh frozen plasma in 0.02 M sodium citrate (for pH 6.8), 10 g. of the just foregoing decanted heparin-SEPHAROSE gel were added.

The mixture was allowed to stand under agitation for 15 minutes, following which the gel (bearing the adsorbate) was decanted onto a filter. 63 percent of the original AHF-activity was left in the non-adsorbed solution as well as 4 percent of the quantity of fibrinogen which was present from the beginning. The AHF-active material then was precipitated by sodium citrate at pH 7.1 as in Example 1. The fibrinogen was eluted from the gel with 2 M NaCl. The yield of fibrinogen was 85 percent.

EXAMPLE 6

AHF and Fibrinogen from Cohn Fraction I-O by Adsorption of the Fibrinogen to Chrondroitin Sulfate-SEPHAROSE Gel Preparation of the cross-linked chondroitin sulfate-SEPHAROSE gel 1 g. of cyanogen bromide was added to an aqueous solution containing 250 mg. of chondroitin sulfate C following which 40 ml. of SEPHAROSE 4B gel was added. The mixture was allowed to stand at pH 11 under agitation for 7 minutes, following which the pH was allowed to drop, and the resulting gel was allowed to stand under agitation for 48 hours. The gel was then washed and ready for use.

Fractionation of Fibrinogen and AHF from Cohn Fraction I-O

About 0.2 g. of freeze-dried Cohn fraction I-O from fresh frozen plasma was dissolved in 20 ml. of citrate buffer (for pH 6.8). Later on 20 ml. of the just above obtained gel were added and the mixture was allowed to stand under agitation for 15 minutes, following which the gel (with its adsorbate) was separated by filtration. Analysis of the non-adsorbed filtrate solution showed that 44 percent of the fibrinogen had been adsorbed on the gel. The AHF-yield was 80 percent. The fibrinogen was desorbed from the gel with 2 M NaCl as in any of Examples 1, 2, 4 or 5.

EXAMPLE 7

AHF and Fibrinogen from Cohn Fraction I-O by Initial Adsorption of the Fibrinogen to Dextran Sulfate-SEPHAROSE Gel Prepared by Epichlorhydrin Induced Cross-linking Preparation of cross-linked dextran sulfate SEPHAROSE gel according to ECD-process 1 liter of SEPHAROSE 4B gel was mixed with 500 ml. of an aqueous solution containing 30 g. dextran sulfate. To this mixture 1 liter of 1 M sodium hydroxide solution, 40 ml. of epichlorhydrin and 10 g. of sodium borohydride were added. The mixture was kept at 60° C. under agitation for 1 hour. The resulting gel was washed with warm water and mixed with 500 ml. of 2 M sodium hydroxide solution and 5 g. of sodium borohydride.

The mixture was autoclaved for 1 hour at 120° C., following which the gel was washed with a solution of lye containing sodium borohydride. Thereafter, glacial acetic acid was added slowly until pH 4. The gel was washed with water and was then ready for use.

Fractionation of Fibrinogen and AHF from Cohn Fraction I-O

Freeze-dried Cohn fraction I-O from fresh frozen plasma was dispersed in the citrate buffer and admixed with the cross-linked dextran sulfate SEPHAROSE 4B gel as in Example 1, and the gel with its adsorbate and the mixed non-adsorbed solution and gel washing were treated as described in Example 1. The non-adsorbed solution obtained after adsorption of the fibrinogen of the gel contained 5 percent of the original protein content and 57 percent of its AHF-activity. The AHF-active material then was precipitated with sodium citrate, for example, as in Example 2. Elution of fibrinogen from the gel was done with 2 M NaCl, and its yield was 90 percent.

EXAMPLE 8

AHF and Fibrinogen from Cohn Fraction I-O by Adsorbing the Fibrinogen to Cross-linked Benzidine Disulfonic Acid Substituted SEPHAROSE Gel Preparation of benzidine disulfonic acid substituted SEPHAROSE gel 250 ml. of SEPHAROSE 4B gel were admixed into 100 ml. water, and 10 g. of cyanogen bromide dissolved in 100 ml. water were added. By addition of a solution of sodium hydroxide the pH was increased to 11.0 and kept at that level under agitation for 7 minutes, following which the treated gel was decanted onto a glass filter and washed with cold water. 14 g. of benzidine-2,2'-disulfonic acid were dissolved in 60 ml. water under simultaneous addition of lye to maintain the pH at 7. The benzidine disulfonic acid solution was added to the gel and their mixture was allowed to stand under agitation at 5° C. over night, followed by washing of the gel with buffer solutions.

Fractionation of Fibrinogen and AHF from Cohn Fraction I-O

About ½ g. of freeze-dried Cohn fraction I-O from fresh frozen plasma was dissolved in 40 ml. water and 10 ml. of suctioned dry gel was added, following which the mixture was agitated for 30 minutes. The gel was filtered off and the fibrinogen was eluted from the gel with 2 M NaCl solution as in any of the earlier examples. By using sodium citrate the AHF-active material was precipitated and removed in the way described in earlier examples. 85 percent of the original fibrinogen had been adsorbed on the matrix, and the AHF yield was 80 percent.

EXAMPLE 9

Derivation of Factors I an VIII from Frozen Plasma

Dextran sulfate-SEPHAROSE gel was prepared according to Example 1 with the exception that the scale was increased to 10 liters of gel.

30 kilos of frozen plasma was thawed, followed by precipitation of Cohn (method 6) fraction I by 8 percent ethanol and centrifugation in a Sharples centrifuge. This fraction I precipitate was cut into pieces and dissolved in 9.6 liters of 0.02M citrate buffer pH 6.8. To the solution was added 180 ml. of 2 percent Al-(OH)$_3$ gel and the mixture was stirred for 30 minutes and the gel was removed by centrifugation.

To the decanted supernatant solution then is added 10 liters of dextran sulfate-SEPHAROSE gel and the mixture is stirred for 30 minutes. The gel then is filtered off and the AHF-active material present in the filtrate is precipitated by addition of sodium citrate as described earlier. The precipitated material contained 0.7 AHF units/mg of protein and it could be dissolved yielding a solution containing 30 units/ml. The yield calculated from the AHF content of the plasma was 34 percent.

The fibrinogen (factor I) then is removed from the dextran sulfate-SEPHAROSE gel by eluting it with 2M NaCl. The fibrinogen obtained was 89 percent pure and its yield was 84 percent.

Examples 1 to 9 illustrate the separate respective isolation of each of the two blood coagulation factors fibrinogen and AHF from a respective single starting material.

These various examples show use of their respective specific starting material source for either one or both of the blood coagulation factors I and VIII. However, any animal blood tissue product containing any of these coagulation factors can be used in the various embodiments of the method of the invention. Such starting blood tissue product can be that of any blood-bearing animal, whether human or bovine or other mammal or other animal, that contains any of theses coagulation factors.

That expression "animal blood tissue product" then embraces primarily blood serum, blood plasma (whether fresh or outdated) as well as any of the blood coagulation factor-containing fractions or concentrates derived from human or bovine or other blood-bearing animal blood, blood serum, or blood plasma, such as the cyroprecipitate, as well as the also earlier available different types of AHF concentrates as the so-called partly low and the partly high concentrated preparations, or the so-called concentrated AHF preparations.

The dextran sulfate used in several of the examples is, as furnished by its supplier (the aforementioned Pharmacia Fine Chemicals), actually sodium dextran sulfate. It commonly is referred to as merely dextran sulfate, not only by the suppliers and in its literature but in other literature. It is supplied as the sodium salt because of its greater stability over time in that form. It may be used in either form in the invention, so that the expression "sulfate dextran" is used herein for the sodium salt form as well.

The SEPHAROSE 4B is not supplied as dry beads. Thus, in those of the examples which mention taking a certain volume of this adsorbing agent, it was used instead in its form, as supplied, as a viscous flowable mixture of the beads in the liquid vehicle as furnished by the supplier but not freely liquid-flowable form.

In the expression "cross-linked dextran sulfate epichlorhydrin-agarose" the portion "epichlorhydrin-agarose" means that the agarose independently was reacted separately with epichlorhydrin. Thus, "cross-linked" in the longer of these two quoted expressions relates, as Example 2 shows, that there also was a cross-linking by a separate cross-linking reaction between the dextran sulfate and the epichlorhydrin-treated agarose.

In addition, Example 7 shows that epichlorhydrin can be used as the cross-linking agent in the reaction medium containing dextran sulfate and agarose (e.g. SEPHAROSE 4B) to provide the cross-linking between the two polysaccharide substances used in preparing the cross-linked water-insoluble gel matrix for the process of the invention, Thus, such gel matrix is referred to in Example 2 as ECD-cross-linked dextran sulfate agarose gel.

The cross-linked benzidine 2,2'-disulfonic acid-agarose of Example 8 can be replaced in its procedure by the corresponding quantity of cross-linked benzidine 2,2'-disulfonic acid-dextran by replacing the SEPHAROSE 4B used in preparing its cross-linked benzidine-agarose gel by the corresponding quantity of dextran.

Generally the specific buffer used in any of the examples as a solvent for the starting animal blood tissue product, or any adsorbate, or any precipitate can be replaced by any other aqueous buffer solution that is compatible with the respective starting blood tissue product, adsorbate, or precipitate and provides the required pH to dissolve the specific tissue product, adsorbate, or precipitate.

The non-adsorbed portion of any starting material solution ordinarily can be washed out of the adsorption mixture or column with a single volume of the starting buffer solution equal to the volume of the gel used in the mixture or column.

The process of the invention enables providing a (i) fibrinogen product containing from about 80 to 90% of actual fibrinogen, and (ii) coagulation factor VIII (AHF) product of a greater purity than that of any other commercially available AHF product.

That gives a valuable advantage by very markedly reducing the amount of liquid containing any of these two coagulation factors to be administered to a patient, with consequent not only saving in cost, but also reduced distress to the patient. For example, the AHF product prepared from fresh plasma by the method of Examples 2 and 9 is available in a concentration of 30 AHF units per ml. That enables administering a highly effective dosage merely as an ordinary injection by a hand syringe and eliminating the need for prolonged continuous infusion from a suspended infusion bottle.

While the invention has been explained by detailed description of certain specific embodiments of it, it is understood that various modifications or substitutions can be made in any of them within the scope of the appended claims which are intended also to cover equivalents of the specific embodiments.

What is claimed is:

1. In a method of isolating at least one of the blood coagulation factors fibrinogen and the antihemophilia factor VIII, from an animal blood tissue product containing fibrinogen or both of these factors, the improvement which comprises (i) contacting a water-insoluble gel matrix adsorbing agent selected from cross-linked dextran sulfate-dextran, cross-linked dextran sulfate-agarose, cross-linked dextran sulfate epichlorhydrin-agarose, dextran sulfate epichlorhydrin-cross-linked agarose, cross-linked chondroitin sulfate, cross-linked heparin-agarose, cross-linked heparin, cross-linked benzidine-2,2'-disulfonic acid-agarose, and cross-linked benzidine-2,2'-disulfonic acid-dextran, with said animal blood tissue product dissolved in an aqueous medium otherwise inert to the therein dissolved content of the said blood tissue product, and (ii) separating the non-adsorbed solution from the gel matrix.

2. A method as claimed in claim 1, wherein said animal blood tissue product is blood.

3. A method as claimed in claim 2, wherein said blood tissue product is human blood.

4. A method as claimed in claim 3, wherein said blood tissue product is either fresh or outdated plasma, or a plasma fraction.

5. A method as claimed in claim 4, wherein said adsorbed factor is fibrinogen.

6. A method as claimed in claim 5, wherein said blood tissue product is a plasma fraction.

7. A method as claimed in claim 6, wherein said blood tissue product is selected from Cohn fraction I-O, Cohn fraction I paste, or Cohn (method 6) fraction I.

8. A method as claimed in claim 4, wherein said blood tissue product contains fibrinogen and the antihemophilia factor, and the fibrinogen is adsorbed therefrom on said adsorbing agent, and the method further comprises separating the gel matrix adsorbing agent bearing said fibrinogen adsorbate from the non-adsorbed remainder of the solution of said blood tissue product.

9. A method as claimed in claim 8, wherein the fibrinogen is separated from said gel matrix adsorbing agent by eluting the fibrinogen from said agent with an aqueous solution of a buffering agent for the fibrinogen and inert to the adsorbing agent, to provide a solution of the fibrinogen in that aqueous buffer solution.

10. A method as claimed in claim 9, wherein the fibrinogen is eluted from said gel matrix adsorbing agent by elution with an aqueous solution of from about 1M to about 2M sodium chloride.

11. A method as claimed in claim 10, wherein the fibrinogen is precipitated from said solution of it by admixing in said solution a water-soluble precipitant for the fibrinogen.

12. A method as claimed in claim 8, wherein the antihemophilia factor is separated from the non-adsorbed remainder of said solution of said blood tissue product.

13. A method as claimed in claim 12, wherein the antihemophilia factor is separated from said non-adsorbed remainder solution by addition of sodium citrate to said remainder solution, and the thus precipitated antihemophilia factor is separated from the resulting mixture.

14. A method as claimed in claim 8, wherein said blood tissue product is Cohn fraction I paste and it is dissolved in an aqueous solution of an inorganic salt solvent buffer for said paste at about pH 6.8, and the adsorbing agent gel matrix is cross-linked dextran sulfate epichlorhydrin treated agarose; and the antihemophilia factor is separated from said non-adsorbed remainder of the solution of said paste by addition of sodium citrate to said non-adsorbed remainder at about pH 7.1.

15. A method as claimed in claim 1, wherein said blood tissue product is brought in contact with said water-insoluble gel matrix adsorbing agent for a time sufficient for the said fibrinogen to be adsorbed by said adsorbing agent; said agent being used in a quantity sufficient to adsorb at least about 15 percent of said fibrinogen from said starting tissue product.

* * * * *

UNITED STATES PATENT AND TRADEMARK OFFICE
CERTIFICATE OF CORRECTION

PATENT NO. 4,022,758

DATED May 10, 1977

INVENTOR(S) Lars-Olov Andersson, Håkan Gunnar Borg, Nanna Forsman, Gunnar Hanshoff, Göran Lindroos, M. Miller-Andersson, E.C. Carling It is certified that error appears in the above-identified patent and that said Letters Patent are hereby corrected as shown below:

Col. 2 line 39, "Blomback" should read -- Blombäck --. Col. 2 line 56, "portions" should read -- proteins --. Col. 3 line 50, "p. 4 lines 10-12" should read -- column 2 lines 37-38 --. Col. 4 line 42, after "agarose" add a colon. Col. 5 line 37, "Pase" should read -- Paste --. Col. 5 line 65, after "4B" insert -- gel --. Col. 6 line 20 "500" should read -- "500" --. Col. 6 line 44, after "4B gel" add a colon. Col. 7 line 11, after "gel" add a colon. Col. 7 line 41, after "process" add a colon. Col. 8 line 10, after "gel" add a colon. Col. 8 line 41, "an" should read -- and --. Col. 8 line 61, after "30" insert --AHF--. Col. 9 line 11, "theses" should read -- these --. Col. 9 line 19, "cyroprecipitate" should read -- cryoprecipitate --.

Signed and Sealed this

Seventeenth Day of October 1978

[SEAL]

Attest:

RUTH C. MASON
Attesting Officer

DONALD W. BANNER
Commissioner of Patents and Trademarks